US00PP35150P2

(12) United States Plant Patent
Guo

(10) Patent No.: US PP35,150 P2
(45) Date of Patent: May 2, 2023

(54) ***KALANCHOE* PLANT NAMED 'KLEKB20040'**

(50) Latin Name: *Kalanchoe blossfeldiana*
Varietal Denomination: KLEKB20040

(71) Applicant: KLEMM + SOHN GMBH & CO. KG, Stuttgart (DE)

(72) Inventor: Huijuan Guo, Kornwestheim (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/881,949

(22) Filed: Aug. 5, 2022

(51) Int. Cl.
*A01H 5/02* (2018.01)
*A01H 6/32* (2018.01)

(52) U.S. Cl.
USPC ..... Plt./341
CPC ..... *A01H 6/324* (2018.05)

(58) Field of Classification Search
USPC ..... Plt./341
CPC ..... A01H 5/02
See application file for complete search history.

(56) References Cited

PUBLICATIONS https://floraland.ro/wp-content/uploads/2022/01/Poinsettia_Kalanchoe_2022_web.pdf; Aug. 25, 2022; 2 pages.*
https://selecta-one.com/en/company/news-detail/new-home-poinsettia-kalanchoe-catalogue-2022; Dec. 20, 2021; 2 pages.*

* cited by examiner

*Primary Examiner* — Kent L Bell
(74) *Attorney, Agent, or Firm* — Weatherly IP Solutions, LLC; James M. Weatherly

(57) ABSTRACT

A new *Kalanchoe* plant particularly distinguished by large, dark red flowers with an entire flower margin, is disclosed.

1 Drawing Sheet

Genus and species: *Kalanchoe blossfeldiana.*
Variety denomination: 'KLEKB20040'.

BACKGROUND OF THE NEW PLANT

The present invention comprises a new and distinct variety of *Kalanchoe*, botanically known as *Kalanchoe blossfeldiana* and hereinafter referred to by the variety name 'KLEKB20040'. 'KLEKB20040' originated from a controlled-cross between the proprietary female *Kalanchoe* variety '1031-1' (unpatented) and the proprietary male *Kalanchoe* variety '724-2' (unpatented).

In May 2018, the two *Kalanchoe* parental lines, the proprietary female *Kalanchoe* variety '1031-1' and the proprietary male *Kalanchoe* variety '724-2' were crossed in De Lier, Netherlands and seeds were obtained. The seeds were sown and plants were grown for evaluation. A single plant was selected in June 2019 and subsequently named 'KLEKB20040'. In July 2019 'KLEKB20040' was first vegetatively propagated by vegetative terminal cuttings in Stuttgart, Germany. 'KLEKB20040' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Dark red flowers; and
2. Large flowers and an entire flower margin.

DESCRIPTION OF THE PHOTOGRAPH

This new *Kalanchoe* plant is illustrated by the accompanying photograph which shows an overall view of the plant.

The photograph is of an approximately 4-month-old plant grown in Stuttgart, Germany in September February 2019.

The colors shown are as true as can be reasonably obtained by conventional photographic procedures.

DESCRIPTION OF THE NEW VARIETY

The following detailed descriptions set forth the distinctive characteristics of 'KLEKB20040'. The data which define these characteristics were collected from asexual reproductions carried out in Stuttgart, Germany. Data was collected on plants grown 16-weeks in Stuttgart, Germany grown in a greenhouse in July 2022. Color references are to The R.H.S. Colour Chart of The Royal Horticultural Society of London (R.H.S.), 5$^{th}$ edition (2007).

Classification:
- *Family.*—Crassulaceae.
- *Botanical.*—*Kalanchoe blossfeldiana.*
- *Designation.*—'KLEKB20040'.

Parentage:
- *Female parent.*—'1031-1' (unpatented).
- *Male parent.*—'724-2' (unpatented).

Plant description:
- *Plant and growth habit.*—Compact, upright, uniformly mounded plant habit; freely flowering habit with numerous cymes positioned above the foliar plane; triangular in shape with rounded crown.
- *Growth habit.*—Moderate.
- *Plant height at flowering.*—About 19.0 cm.
- *Plant diameter at flowering.*—About 21.0 cm.

Branching:
- *Branching habit.*—Freely branching habit with about twelve lateral branches developing per plant.
- *Lateral branch description.*—Length: 8.0 cm to 15.0 cm. Diameter: 7.0 cm. Internode length: 1.0 cm. Aspect: Mostly upright. Strength: Moderately strong. Texture: Smooth, glabrous. Color: Developing: RHS 143B. Developed: RHS 143B.

Leaf description:

*Arrangement.*—Opposite, single; generally symmetrical.

*Quantity of leaves per lateral branch.*—1 to 5 pairs.

*Length.*—About 10.0 cm.

*Width.*—About 6.5 cm.

*Shape.*—Ovate.

*Apex.*—Obtuse.

*Base.*—Obtuse.

*Margin.*—Broadly crenate.

*Texture.*—Upper surface: Smooth, glabrous, coriaceous, succulent, glossy. Lower surface: Smooth, glabrous, coriaceous, succulent, matte.

*Venation pattern.*—Pinnate.

*Leaf venation color.*—Upper surface: RHS 139A. Low surface: RHS 137C.

*Color.*—Developing leaves: Upper surface: RHS 147A. Lower surface: RHS 138A. Fully developed leaves. Upper surface: RHS 147A. Lower surface: RHS 138A.

Petioles:

*Length.*—0.8 cm.

*Diameter.*—0.5 cm to 0.8 cm.

*Strength.*—Moderately strong.

*Texture.*—Smooth, glabrous, coriaceous, succulent.

*Color.*—Upper surface: RHS 147A. Lower surface: RHS 138A.

Flower description:

*Flower arrangement and habit.*—Single type flowers arranged in axillary cymes; uniform and freely flowering habit, continuously for at least 8 weeks.

*Fragrance.*—No.

*Natural flowering season.*—Initiate and develop flowers under short day/long night conditions or during November and December in the Northern Hemisphere; buds and flowers can also be induced under artificial short day/long night conditions with around 14 hours darkness.

*Time to flower.*—Early flowering habit, plants begin flowering around 12 weeks after potting.

*Post-production longevity.*—Excellent post-production longevity, plants maintain good foliage and flower substance.

*Flower diameter.*—1.5 cm.

*Flower length (height).*—1.4 cm.

*Flower bud.*—Length: 1.2 cm. Diameter: 0.2 cm. Shape: Initially oblong, becoming tubular ovoid with development. Texture: Smooth, glabrous, glossy. Color: RHS 60B.

Petals:

*Arrangement.*—Four in a single whorl.

*Length.*—1.0 cm.

*Width.*—0.7 cm.

*Aspect.*—Flat.

*Shape.*—Ovate to round.

*Apex.*—Acute.

*Base.*—Obtuse.

*Margin.*—Entire.

*Texture.*—Upper surface: Smooth, glabrous, glossy. Lower surface: Smooth, glabrous, glossy.

*Color.*—When opening: Upper surface: RHS 45A. Lower surface: RHS 45B. Fully opened: Upper surface: RHS 46A. Lower surface: RHS 46B.

Sepals:

*Appearance.*—Four in a single whorl.

*Length.*—0.7 cm to 0.9 cm.

*Width.*—0.2 cm.

*Shape.*—Oblong, pointed.

*Apex.*—Acute.

*Base.*—Obtuse.

*Margin.*—Entire.

*Aspect.*—Upright.

*Texture.*—Upper surface: Smooth, glabrous, glossy. Lower surface: Smooth, glabrous, glossy.

*Color.*—Upper surface: RHS 143C. Lower surface: RHS 143C.

Peduncles:

*Length.*—0.6 cm.

*Diameter.*—0.1 cm.

*Aspect.*—Erect.

*Strength.*—Moderately strong.

*Texture.*—Smooth and glabrous.

*Color.*—RHS 137A.

Reproductive organs:

*Androecium.*—Stamen number: Eight per flower. Filament color: RHS 160C. Anther length: 0.1 cm to 0.3 cm. Anther shape: Elliptic. Anther color: RHS 154C. Amount of pollen: Scarce. Pollen color: RHS 13B.

*Gynoecium.*—Pistil number: Four. Pistil length: 0.7 cm. Style length: 0.2 cm. Style color: RHS 141D. Stigma shape: Flat. Stigma color: RHS 141D. Ovary color: RHS 141C.

Seeds:

*Quantity per flower.*—Up to 20 seeds per flower.

*Length.*—0.01 cm.

*Diameter.*—0.005 cm.

*Texture.*—Rough.

*Color.*—RHS 166C.

Temperature tolerance: Plants have been observed to tolerate temperatures from 10° C. to 40° C., suitable for garden use.

Disease and pest/insect resistance: Plants have been observed to have tolerance to Powdery Mildew (*Erysiphe cichoraceaum*).

COMPARISON WITH PARENTAL LINES AND KNOWN VARIETY

'KLEKB20040' is distinguished from its parents as described in Table 1:

TABLE 1

Comparison with Parental Lines

| Characteristic | Variety 'KLEKB20040' | Female parent | Male Parent |
|---|---|---|---|
| Flower color | Dark red | Red | Medium red |

'KLEKB20040' can be compared to the commercial variety 'Lipstick' (unpatented). Differences between the two varieties are described in Table 2:

TABLE 2

Comparison with Similar Variety

| Trait | 'KLEKB20040' | Commercial line 'Lipstick' |
|---|---|---|
| Leaf margin | The new Kalanchoe variety has an entire leaf margin. | Lipstick has erose leaf margin. |
| Flower diameter | The new Kalanchoe variety has the flower diameter 1.5 cm | Lipstick has the flower diameter about 1-1.5 cm. |

I claim:

1. A new and distinct cultivar of *Kalanchoe* Plant Named 'KLEKB20040' as described and illustrated herein.

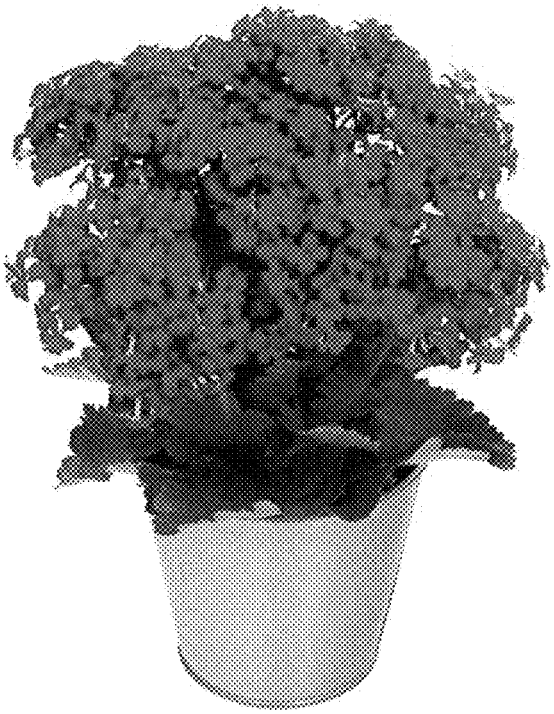

* * * * *